United States Patent
Clarida et al.

(10) Patent No.: US 11,880,976 B2
(45) Date of Patent: Jan. 23, 2024

(54) IMAGE RETENTION AND STITCHING FOR MINIMAL-FLASH EYE DISEASE DIAGNOSIS

(71) Applicant: Digital Diagnostics Inc., Coralville, IA (US)

(72) Inventors: Warren James Clarida, Iowa City, IA (US); Ryan Earl Rohret Amelon, University Heights, IA (US); Abhay Shah, Burlington, IA (US); Jacob Patrick Suther, Burlington, IA (US); Meindert Niemeijer, Coralville, IA (US); Michael David Abramoff, University Heights, IA (US)

(73) Assignee: Digital Diagnostics Inc., Coralville, IA (US)

( * ) Notice: Subject to any disclaimer, the term of this patent is extended or adjusted under 35 U.S.C. 154(b) by 312 days.

(21) Appl. No.: 17/202,199

(22) Filed: Mar. 15, 2021

(65) Prior Publication Data

US 2021/0295516 A1    Sep. 23, 2021

Related U.S. Application Data

(60) Provisional application No. 62/992,041, filed on Mar. 19, 2020.

(51) Int. Cl.
   *G06K 9/00*    (2022.01)
   *G06T 7/00*    (2017.01)
   (Continued)

(52) U.S. Cl.
   CPC ........... *G06T 7/0014* (2013.01); *G16H 30/40* (2018.01); *G16H 50/20* (2018.01); *G16H 50/30* (2018.01);
   (Continued)

(58) Field of Classification Search
   None
   See application file for complete search history.

(56) References Cited

U.S. PATENT DOCUMENTS

| 8,885,901 B1 | 11/2014 | Solanki et al. |
| 2019/0110753 A1 | 4/2019 | Zhang et al. |

(Continued)

OTHER PUBLICATIONS

PCT International Search Report and Written Opinion, PCT Application No. PCT/US2021/022425, dated Jun. 3, 2021, 13 pages.

*Primary Examiner* — Wei Wen Yang
(74) *Attorney, Agent, or Firm* — Fenwick & West LLP

(57) ABSTRACT

Systems and methods are provided herein for minimizing retinal exposure to flash during image gathering for diagnosis. In an embodiment, a system captures a plurality of retinal images of different retinal regions. The system determines that a first portion of a first image does not meet a criterion while a second portion of the first image does meet the criterion, identifies a portion of the retina depicted in the first portion that does not meet the criterion, and determines whether the portion of the retina is depicted in a third portion of a second image and whether the third portion meets the criterion. Responsive to determining that the third portion meets the criterion, the system performs the diagnosis. Responsive to determining that the portion of the retina is not depicted in the second image, the system captures an additional image of the retinal region.

19 Claims, 6 Drawing Sheets

(51) Int. Cl.
  *G16H 30/40* (2018.01)
  *G16H 50/30* (2018.01)
  *G16H 50/20* (2018.01)
(52) U.S. Cl.
  CPC .............. *G06T 2207/10016* (2013.01); *G06T 2207/30041* (2013.01)

(56) References Cited

U.S. PATENT DOCUMENTS

2019/0117064 A1* 4/2019 Fletcher ............ H04M 1/72409
2021/0290056 A1* 9/2021 Karandikar ............ A61B 3/117

* cited by examiner

IMAGE RETENTION AND STITCHING FOR MINIMAL-FLASH EYE DISEASE DIAGNOSIS

CROSS-REFERENCE TO RELATED APPLICATIONS

This application claims the benefit of U.S. Provisional Patent Application Ser. No. 62/992,041, "Image Retention and Stitching for Minimal-Flash Eye Disease Diagnosis," filed Mar. 19, 2020, the disclosure of which is hereby incorporated by reference herein in its entirety.

BACKGROUND

This invention relates generally to autonomous diagnosis of retinal abnormalities, and more specifically to image retention to reduce a need to flash a patient's retina.

Autonomous systems for diagnosing retinal abnormalities capture images of a patient's retina (interchangeably used with the word fundus herein), and analyze those images for abnormalities. Typically, images of different parts of the retina are captured (e.g., a fovea-centered image, and an optic disc-centered image). When captured images are insufficient for performing diagnosis, further images are captured until a sufficient image of each part of the retina is obtained. Repeated exposure to flash by an imaging device may cause further pupil restriction making successful imaging less likely following each flash. Thus, reducing the need for further images to be captured until a sufficient image is captured reduce a number of flashes and reduce a need to take myriad pictures, or force a patient to wait to be diagnosed until the pupil recovers to normal dilation. Additionally, reducing the need for further images might enable faster diagnosis, in that the number of flashes that cause pupil restriction to drastically increase would be less likely to be reached in a sitting, thus preventing a need to delay patient diagnosis until such a time that it is again likely to yield a viable image to flash the patient's eye.

SUMMARY

Systems and methods are provided herein for reducing a need to re-flash a patient's eye to capture an image of a retinal region where a prior-captured image was insufficient. As an example, two images may be captured to perform diagnosis on a patient's right eye—a fovea-centered image, and an optic disc-centered image. There is some overlap between the portions of the retina depicted in these two images. Where a region of the retina depicted in one of the images is not useable for any reason (e.g., over- or under-exposure), rather than re-capture the image, the system may determine whether the same region is depicted, without the same defect, in the other image. Should the region be useable from the other image, the system would avoid a need to re-flash the patient's right eye to capture another image of that region, and instead may stitch together portions of the two images in order to perform the diagnosis.

In order to minimize retinal exposure to flash during image gathering for diagnosis, in an embodiment, a retinal image pre-processing tool captures a plurality of retinal images (e.g., by instructing an imaging device to take images and send them to the retinal image pre-processing tool). Each retinal image may correspond to a different retinal region of a plurality of retinal regions (e.g., fovea-centered and optic disc-centered). The retinal image pre-processing tool may determine that a first portion of a first image (e.g., fovea-centered) does not meet a criterion (e.g., the image is over- or under-exposed, has shadows or other artifacts, etc.) while a second portion (e.g., optic disc-centered) of the first image does meet the criterion (e.g., the second image is properly exposed).

The retinal image pre-processing tool may identify a portion of the retina depicted in the first portion that does not meet the criterion, and may determine that the same portion of the retina is depicted in a third portion of the second image. The retinal image pre-processing tool may determine whether the third portion meets the criterion. Responsive to determining that the third portion meets the criterion, a diagnosis may be performed using the plurality of retinal images. Responsive to determining that the portion of the retina is not depicted in the second image, the retinal image pre-processing tool may capture an additional image of the retinal region depicted in the first image.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION (a) Environment Overview

Figure 1:
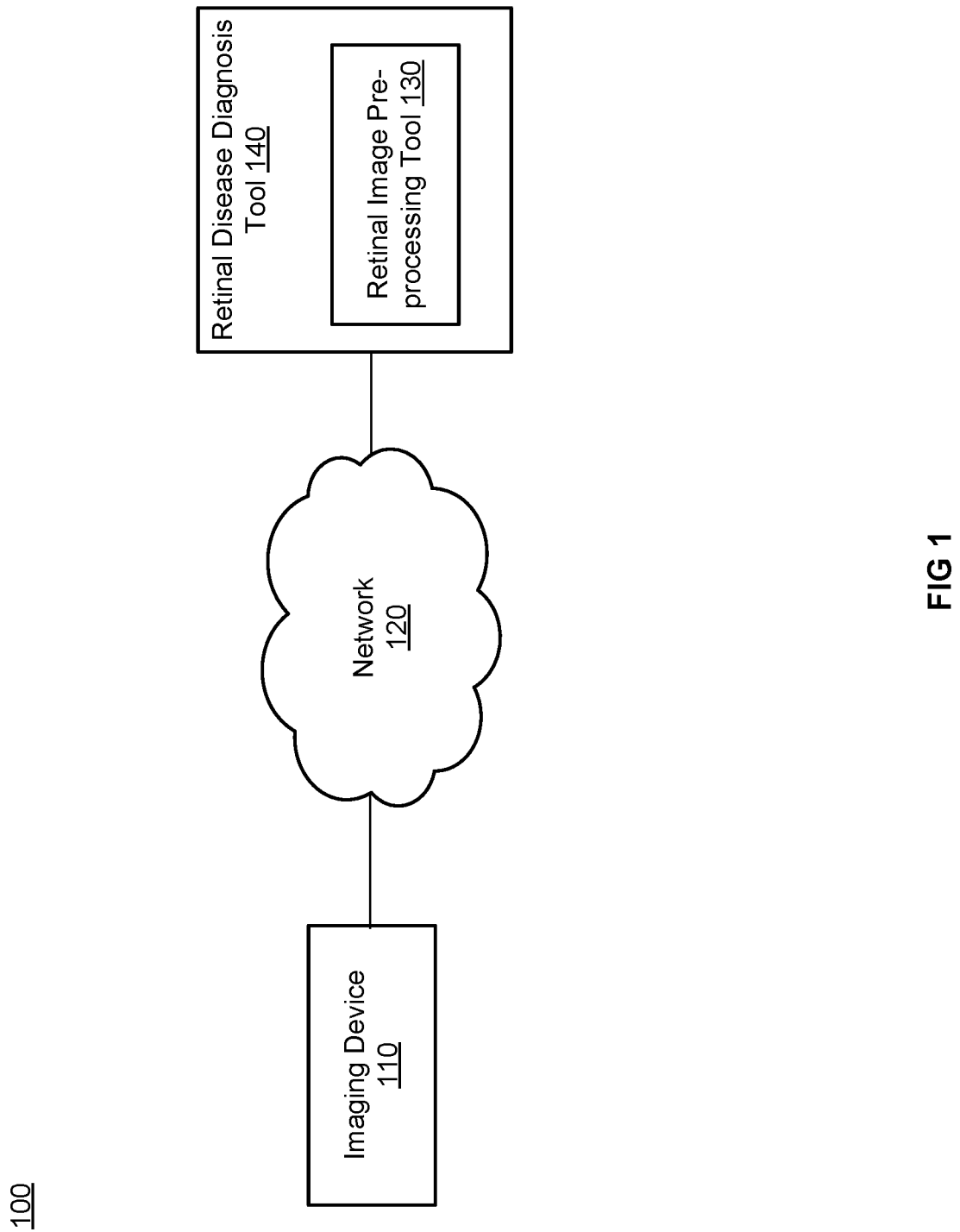
FIG. 1 is an exemplary block diagram of system components in an environment for utilizing a retinal image pre-processing tool, in accordance with one embodiment.

FIG. 1 is an exemplary block diagram of system components in an environment for utilizing a retinal image pre-processing tool, in accordance with one embodiment. Environment 100 includes imaging device 110, network 120, retinal image pre-processing tool 130, and retinal disease diagnosis tool 140. Imaging device 110 is a device configured to capture one or more images of a retina of a patient's eye. Imaging device 110 may be caused to capture such images through manual operation, autonomously as instructed by computer program instructions or external signals (e.g., received from retinal pigmentation determination tool 130), or a combination thereof. Examples of what these images may look like, and how they are derived, are described in commonly-owned U.S. patent application Ser. No. 15/466,636, filed Mar. 22, 2017, the disclosure of which is hereby incorporated by reference herein in its entirety. Other examples are described with respect to FIG. 5 of the instant disclosure.

After capturing an image, imaging device 110 transmits the image to retinal disease diagnosis tool 140. Retinal disease diagnosis tool 140 may take one or more images as input, and may fully autonomously output a diagnosis based on the input using a machine learning model. Retinal disease diagnosis tool 140 autonomously analyzes retinal images and determines, using machine learning analysis of biomarkers therein, a diagnosis. The diagnosis may specifically be a determination that the user has a particular disease, such as diabetic retinopathy, or may be a determination that the user likely has a disease and should thus see a doctor for confirmation and treatment. The manners in which retinal disease diagnosis tool 140 performs the analysis and determines a diagnosis are further discussed in commonly-owned U.S. Pat. No. 10,115,194, issued Oct. 30, 2019, the disclosure of which is hereby incorporated by reference herein in its entirety.

Prior to performing diagnosis, retinal disease diagnosis tool 140 may have retinal image pre-processing tool 130 determine whether the image(s) captured by imaging device 110 are sufficient for performing diagnosis. Manners in which retinal image pre-processing tool 130 performs this analysis are described in further detail with respect to FIG. 3 below. While depicted as a component of retinal disease diagnosis tool 140, retinal image pre-processing tool 130 may be a standalone entity that receives the images, vets the images for sufficiency, and then transmits the images to retinal disease diagnosis tool 140 if the images are sufficient for diagnosis. Retinal image pre-processing tool 130 and/or retinal disease diagnosis tool 140 may be instantiated on one or more servers. Moreover, retinal image pre-processing tool 130 and/or retinal disease diagnosis tool 140 may be instantiated, in whole or in part, at imaging device 110, thus eliminating some or all need for communications traffic over network 120.

(b) Exemplary Imaging Device Components

Figure 2:
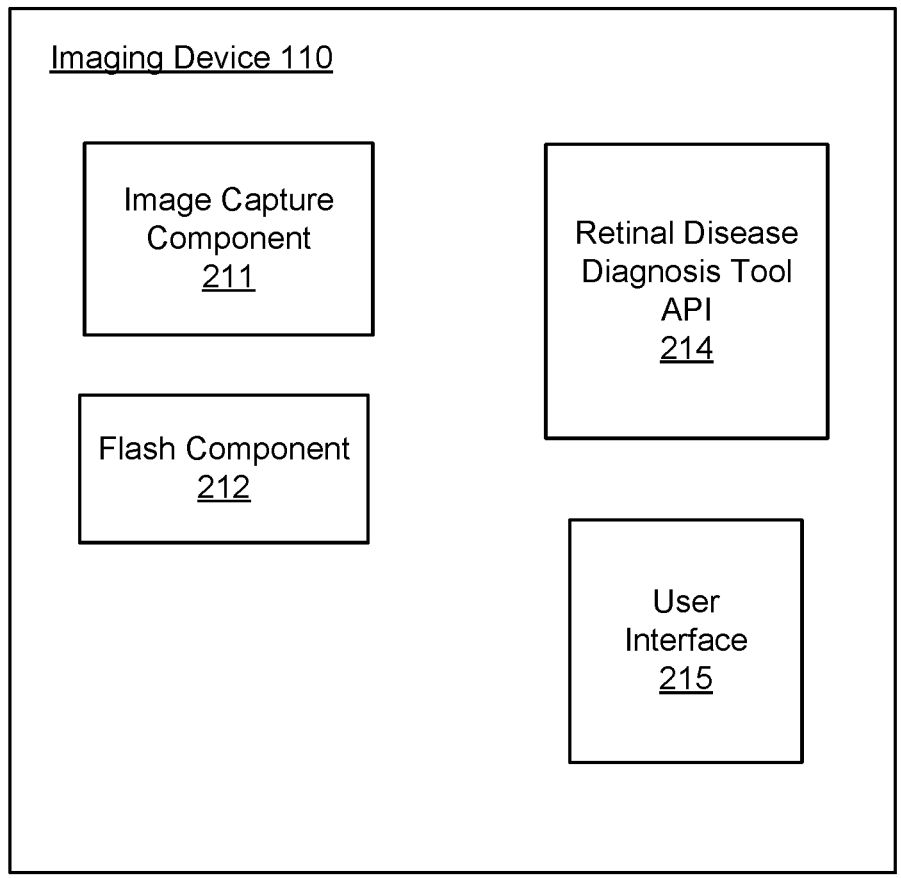
FIG. 2 is an exemplary block diagram of modules and components of an imaging device, in accordance with one embodiment.

FIG. 2 is an exemplary block diagram of modules and components of an imaging device, in accordance with one embodiment. Imaging device 110 includes image capture component 211, flash component 212, retinal disease diagnosis tool application protocol interface (API) 214, and user interface 215. While not depicted, imaging device 110 may include other components, such as on-board instantiations of either or both of retinal image pre-processing tool 130 and retinal disease diagnosis tool 140, and any components thereof. Imaging device 110 may include any databases or memory for performing any functions described herein. Imaging device 110 may exclude some depicted components as well.

Image capture component 211 may be any sensor configured to capture an image of a patient's retina. For example, a specialized lens may be used to capture the image of the patient's retina. Flash component 212 may be any component capable of illuminating a patient's retina during the image capture by image capture component 211, and may be configured to emit light in concert with an image capture operation of image capture component 211.

Retinal disease diagnosis tool API 214 interfaces with retinal disease diagnosis tool 130 to translate commands from retinal image pre-processing tool 130 to imaging device 110. Exemplary commands may include a command to capture or re-capture an image, a command to adjust an intensity of light emitted by flash component 212, and the like. These commands and how they are generated are discussed in further detail with reference to FIG. 3 below.

User interface 215 is an interface with which an operator of imaging device 110 may command imaging device 110 to perform any function it is capable of performing, such as capturing images, adjusting flash intensity, and the like. User interface 215 may be any hardware or software interface, and may include physical components (e.g., buttons) and/or graphical components (e.g., on a display, such as a touch screen display). User interface 215 may be located on imaging device 110, may be a device peripheral to imaging device 110, or may be located on a device separated from imaging device 110 by network 120, thus enabling remote operation of imaging device 110. An exemplary user interface is shown and discussed in further detail with respect to FIG. 5.

(c) Exemplary Retinal Image Pre-Processing Tool Components

Figure 3:
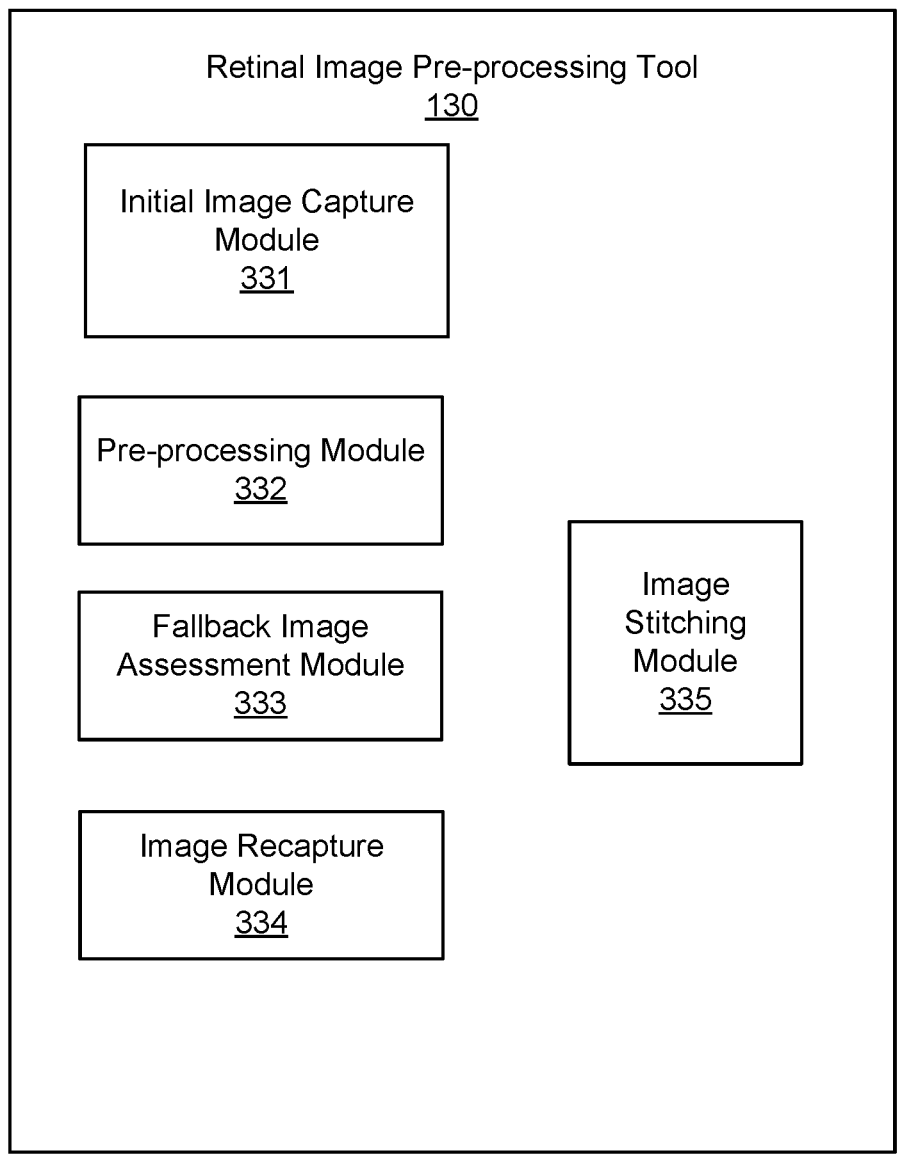
FIG. 3 is an exemplary block diagram of modules and components of a retinal image pre-processing tool, in accordance with one embodiment.

FIG. 3 is an exemplary block diagram of modules and components of a retinal image pre-processing tool, in accordance with one embodiment. Retinal image pre-processing tool 130 includes initial image capture module 331, pre-processing module 232, fallback image assessment module 233, image recapture module 234, and image stitching module 235. While not depicted, retinal image pre-processing tool 110 may include other components such as additional modules, and any databases or memory for performing any functions described herein. Retinal image pre-processing tool 130 may exclude some depicted components as well.

Initial image capture module 331 captures retinal images of one or both of a patient's eyes. The term capture, as used herein, may refer to causing the image to be taken—that is, "capturing" may involve commanding, from a remote device or server, imaging device 110 to take an image and transmit the image to initial image capture module 331 over network 120. Alternatively, where initial image capture module 331 resides on imaging device 110, initial image capture module 331 may capture the image by commanding the imaging device to take the image and route it internally to pre-processing module 332.

The initial images that are captured by initial image capture module 331 may include images of different portions of a patient's retina. The images of different portions, when used as inputs together to one or more machine learning models of retinal disease diagnosis tool 140, result in an output of a diagnosis of retinal disease. The retinal regions may be pre-defined. For example, an administrator of retinal disease diagnosis tool 140 may indicate that images of certain retinal regions are to be captured for diagnosis. The regions may be defined as a fovea-centered image, and as an optic disc-centered image. Thus, initial image capture module 331 may capture images for one or both of the patient's eyes that are centered around those specified retinal regions.

In an embodiment, the images that are captured may be multi-frame videos over a span of time. For example, similar to "live photos," frames may be captured from a moment where a flash is first emitted, until a moment where the flash completely dissipates, where the frames, if displayed sequentially, would form a video. Capturing multiple frames improves the chances that one of the frames includes a portion of a retina depicted by the image that satisfies pre-processing criteria (described below), even if that portion in another of the frames does not satisfy that criteria. For example, following from the flash example, if under-exposure, over-exposure, or shadowing caused by one intensity of flash were corrected when the flash were adjusted to another intensity (e.g., 0.05 seconds later the flash is dims as it is being shut off), then a portion of the retina depicted in the frame at the other intensity may be used to satisfy the criteria.

Pre-processing module 332 is used to determine whether the captured images are sufficient for input into the machine learning model. Sufficiency may also be defined by an administrator, and may be based on parameters such as under-exposure (e.g., the image was captured using too low of an intensity of flash), over-exposure (e.g., the image was captured using too high an intensity of flash), blurriness (e.g., the patient moved when the image was captured, causing the image to be unclear), shadows, and/or any other specified parameters. Criteria may be established based on these parameters for determining whether the image is sufficient—for example, the image must be within a certain range of exposure, and/or landmarks (e.g., a border of the optic disc) must be sufficiently narrow (where a wide border indicates blurriness). Pre-processing module 332 compares the parameters of the images to the criteria to determine whether each image is sufficient for input into the machine learning model.

In an embodiment, where pre-processing module 332 determines that an image is insufficient for input into the machine learning model, retinal image pre-processing tool 130 may command that the insufficient image is recaptured. This embodiment, however, causes disadvantages where patient health may be impacted in that extra flashes of the patient's eye are required. Technological disadvantages occur as well, as extra bandwidth and processing power is required to capture and re-transmit the images to retinal image pre-processing tool 130. Fallback image assessment module 333 is used in an embodiment to determine whether diagnosis can be performed notwithstanding the insufficiency of a given image, without recapturing the image.

Fallback image assessment model 333 identifies one or more depicted portions of a retina in an image that do not meet one or more criteria. For example, an image may be partially over- or under-exposed because retinal pigmentation in the patient's retina is inconsistent, leading to a consistent level of flash causing proper exposure in some parts of a patient's retina, while causing improper exposure in other parts of the patient's retina. As another example, an image may have shadowing that could obscure one or more biomarkers depicted portions of the retina, while leaving the remainder of the image with sufficient quality. Thus, portion(s) that do, and/or portion(s) that do not, meet the one or more criteria may be isolated by fallback image assessment model 333. Fallback image assessment model 333 may identify these portions by examining on any basis (e.g., pixel-by-pixel, quadrant by quadrant, region by region, etc.) for portions of the image that do and do not satisfy the criteria.

Where portions of the retina depicted by an image are determined to be insufficient, fallback image assessment model 333 examines one or more other images captured by initial image capture module 331 to determine whether that portion is recoverable without re-capturing the image to cure the insufficiency. For example, if a portion of the retina depicted in a fovea-centered image of a patient's retina is insufficient, fallback image assessment model 333 may determine whether that same portion of the retina is depicted in an optic disc-centered image of the patient's retina that was also captured during initial image capture. Another example may include assessing whether a frame of a multi-frame video of which the insufficient image is a part may be used. Because fallback image assessment model 333 assesses whether each captured image is sufficient for diagnosis, fallback image assessment model 333 is able to readily determine, if the same portion of the retina is depicted in another image, whether that same portion is of sufficient quality. Where the same portion is of sufficient quality, fallback image assessment module 333 determines that recapture of the image is not necessary, as a fallback image is available. Where fallback image assessment module 333 determines that the same image of the retina is not depicted in another image at sufficient quality, fallback image assessment module 333 determines that the image is to be recaptured. In an embodiment, two or more images may together be used as fallbacks for a single image, where different insufficient portions of the image are repaired by portions from the two or more fallback images.

Image recapture module 334 recaptures images where images are insufficient, and, in some embodiments, where there is no adequate fallback image to cure the insufficiency. Other than being used to capture images of already-captured regions of the retina, image recapture module 334 functions in the same manner as image capture module 331.

Image stitching module 335 stitches together sufficient portions of an image with replacement matter for insufficient portions of the image, the replacement matter being from a fallback image. The term stitching, as used herein, refers to either an actual, or logical, aggregation of portions from two images. Actual stitching refers to generating a composite image that includes portions from at least two images. Logical stitching refers to taking different portions from different images and using those separate portions for diagnosis. For example, the portions are separately input into the machine learning model without generating a composite image, and a diagnosis is output therefrom. As another example, sufficient portions of an image, while discounting insufficient portions of that image, may be used to generate a first analysis. A fallback image may have a portion corresponding to the first image's insufficient portion(s) that is used to generate a second analysis. The two analyses may be used to perform the diagnosis (e.g., by inputting the analyses, with or without the images themselves, into the machine learning model). In an embodiment, image stitching module 335 may weigh an insufficient image quality area based on prevalence of biomarkers in those area with respect to distance from anatomical markers like fovea and optical disc to allow for higher confidence in processing those exams even if there is some area in the fovea of the stitched image with insufficient image quality. Such a weighting can be based on training of a random forest, ANN, and the like, on a representative dataset to learn and weigh the importance of various sufficient image quality areas in the fovea. While image stitching module 335 is depicted as a module of retinal image pre-processing tool 130, image stitching module 335 may instead, in whole or in part, be a module of retinal disease diagnosis tool 140.

(d) Exemplary Computing Machine Architecture

Figure 4:
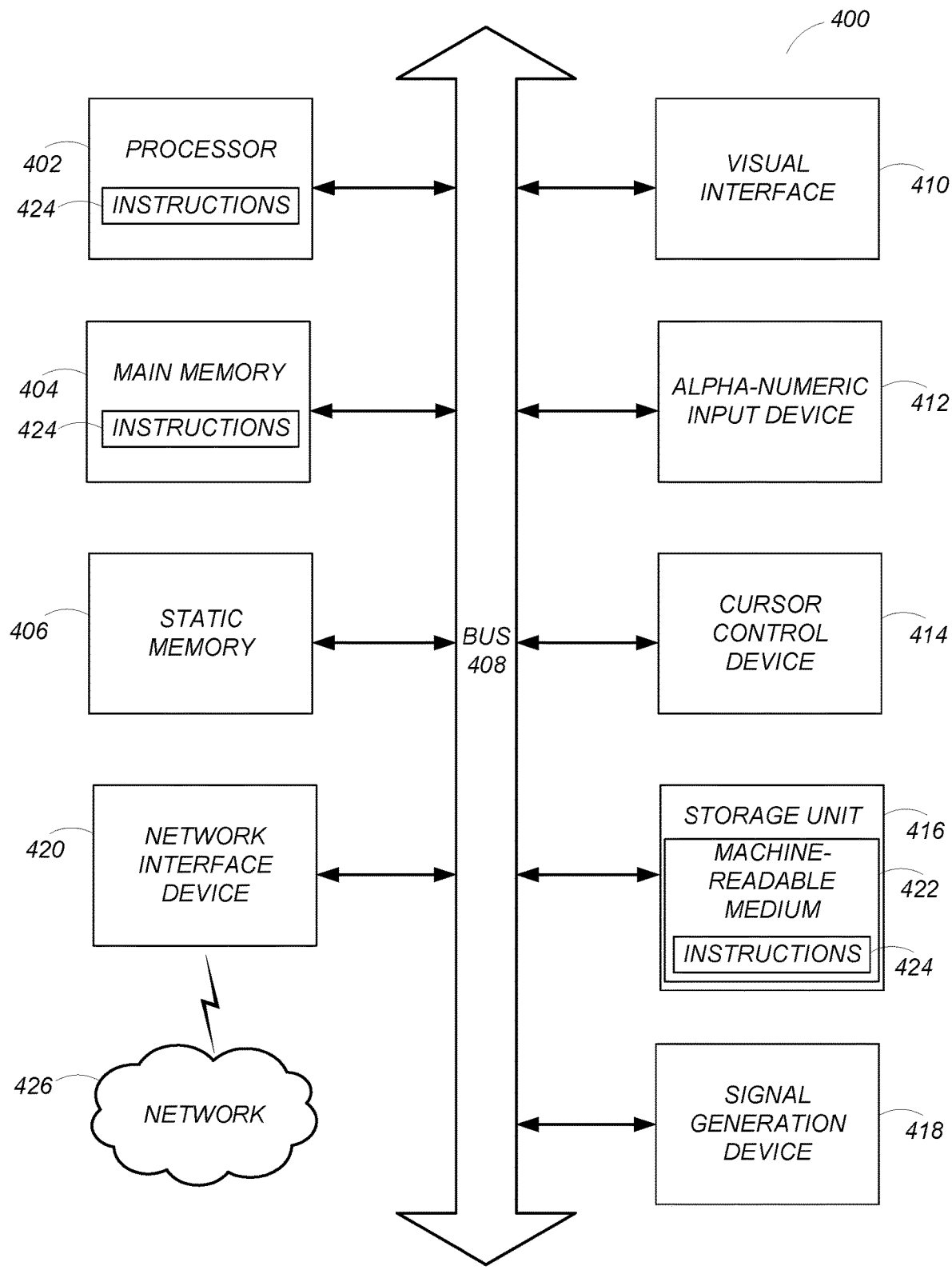
FIG. 4 is a block diagram illustrating components of an example machine able to read instructions from a machine-readable medium and execute them in a processor (or controller).

FIG. 4 is a block diagram illustrating components of an example machine able to read instructions from a machine-readable medium and execute them in a processor (or controller). Specifically, FIG. 4 shows a diagrammatic representation of a machine in the example form of a computer system 400 within which program code (e.g., software) for causing the machine to perform any one or more of the methodologies discussed herein may be executed. The program code may be comprised of instructions 424 executable by one or more processors 402. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 424 (sequential or otherwise) that specify actions to be taken by that machine. Further, while only a single machine is illustrated, the term "machine" shall also be taken to include any collection of machines that individually or jointly execute instructions 124 to perform any one or more of the methodologies discussed herein.

The example computer system 400 includes a processor 402 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 404, and a static memory 406, which are configured to communicate with each other via a bus 408. The computer system 400 may further include visual display interface 410. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 410 may include or may interface with a touch enabled screen. The computer system 400 may also include alpha-numeric input device 412 (e.g., a keyboard or touch screen keyboard), a cursor control device 414 (e.g., a mouse, a trackball, a joystick, a motion sensor, or other pointing instrument), a storage unit 416, a signal generation device 418 (e.g., a speaker), and a network interface device 420, which also are configured to communicate via the bus 408.

The storage unit 416 includes a machine-readable medium 422 on which is stored instructions 424 (e.g., software) embodying any one or more of the methodologies or functions described herein. The instructions 424 (e.g., software) may also reside, completely or at least partially, within the main memory 404 or within the processor 402 (e.g., within a processor's cache memory) during execution thereof by the computer system 400, the main memory 404 and the processor 402 also constituting machine-readable media. The instructions 424 (e.g., software) may be transmitted or received over a network 426 via the network interface device 420.

While machine-readable medium 422 is shown in an example embodiment to be a single medium, the term "machine-readable medium" should be taken to include a single medium or multiple media (e.g., a centralized or distributed database, or associated caches and servers) able to store instructions (e.g., instructions 424). The term "machine-readable medium" shall also be taken to include any medium that is capable of storing instructions (e.g., instructions 424) for execution by the machine and that cause the machine to perform any one or more of the methodologies disclosed herein. The term "machine-readable medium" includes, but not be limited to, data repositories in the form of solid-state memories, optical media, and magnetic media.

(e) Exemplary Images and User Interface

Figure 5:
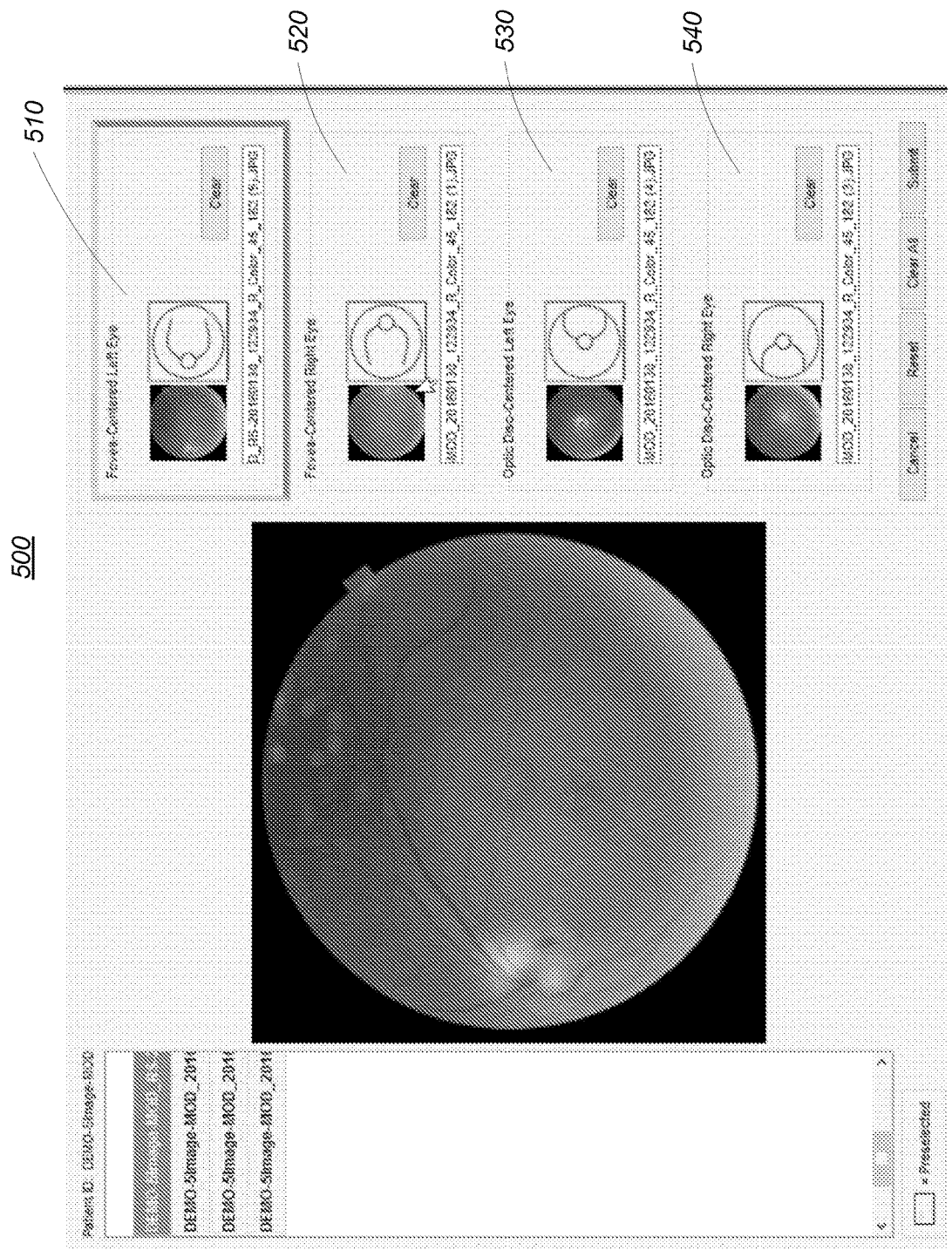
FIG. 5 depicts exemplary images of a patient's eyes, in accordance with one embodiment.

FIG. 5 depicts exemplary images of a patient's eyes, in accordance with one embodiment. User interface 500 may be displayed as part of user interface 215 to an operator of imaging device 110. User interface 500 includes images 510, 520, 530, and 540. As depicted, the patient has had two images captured of each eye—namely, a fovea-centered image and an optic disc-centered image. These images, as depicted, are merely exemplary; any parameters may be used to dictate where an image is to be centered, as input by an operator of imaging device 110 and/or an administrator who defines what images are necessary to perform a diagnosis. Moreover, while two images are used in the example depicted, any number of images may be used. Where images are centered around the optic disc and the fovea, a portion of the images will overlap, and thus, each image may be used as a fallback for each other image if any of the overlapping portion of one image does not meet specified criteria.

Figure 6:
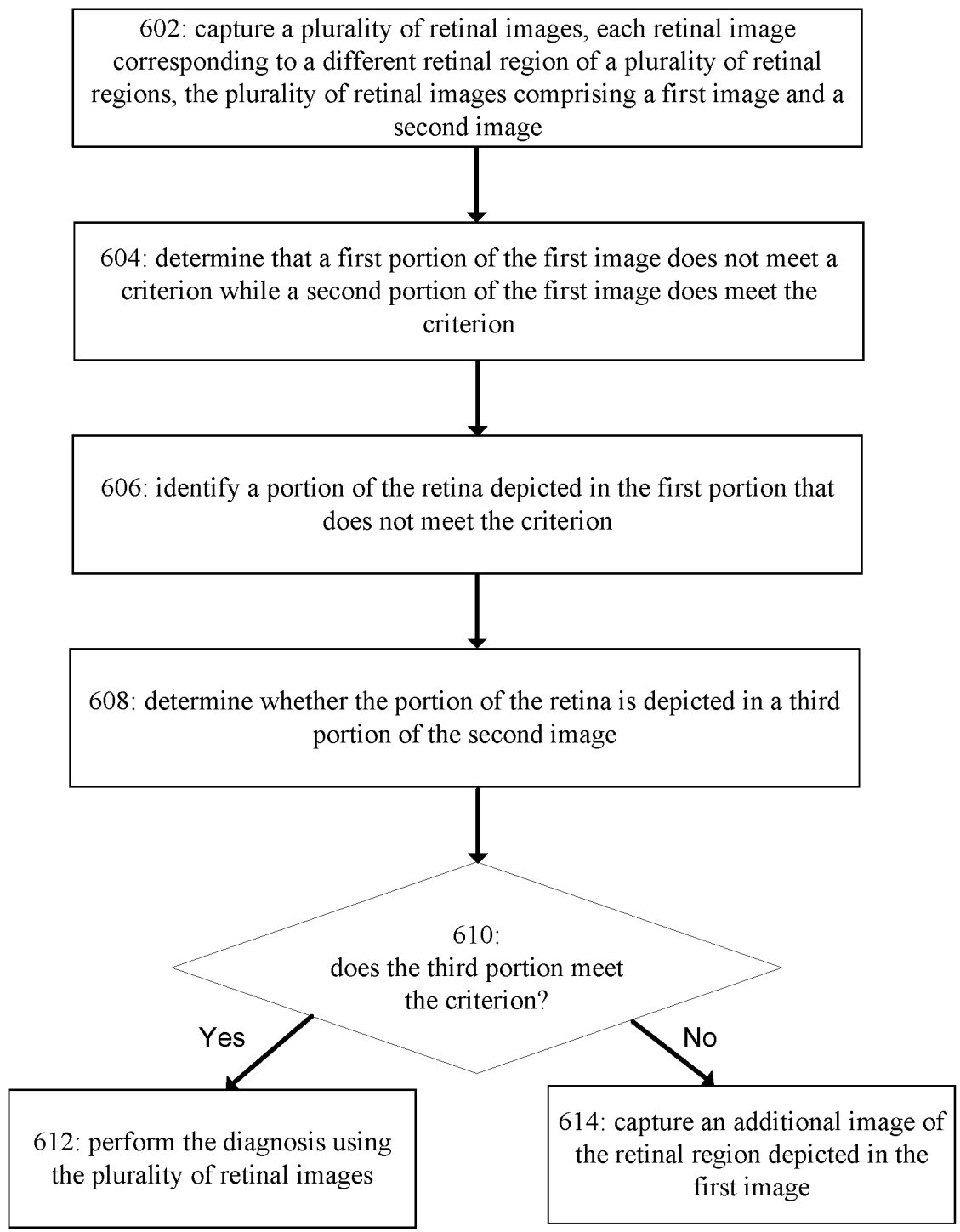
FIG. 6 depicts an exemplary flow chart for minimizing retinal exposure to flash during image gathering for diagnosis, in accordance with one embodiment.

(f) Exemplary Data Flow for Minimizing Retinal Exposure to Flash During Mage Gathering for Diagnosis FIG. 6 depicts an exemplary flow chart for minimizing retinal exposure to flash during image gathering for diagnosis, in accordance with one embodiment. Process 600 begins with one or more processors (e.g., processor 402) of a device used to run retinal image pre-processing tool 130 capturing 602 (e.g., using initial image capture module 331) a plurality of retinal images, each retinal image corresponding to a different retinal region of a plurality of retinal regions, the plurality of retinal images comprising a first image and a second image. The plurality of retinal images may include, for example, fovea-centered and optic disc-centered images for each eye. The first image may be fovea-centered image 510 of the patient's left eye, and the second image may be optic disc-centered image 530 of the patient's left eye, and the different retinal regions may correspond to the retinal region in which each image is centered.

Retinal image pre-processing tool 130 determines 604 that a first portion of the first image does not meet a criterion while a second portion of the first image does meet the criterion. For example, due to retinal striations, over-exposure, under-exposure, shadowing, or other issues, a portion of fovea-centered left eye image 510 is determined to be insufficient, while the remainder of fovea-centered left eye image 510 is determined to be sufficient. The sufficiency determination may be performed by pre-processing module 332 using any manner described herein.

Retinal image pre-processing tool 130 identifies 606 a portion of the retina depicted in the first portion that does not meet the criterion. That is, the portion of the retina itself may be depicted at a different coordinate of a fallback image, and thus, it is the portion of the retina (rather than of the image) that is identified. Fallback image assessment module 333 may perform this determination in any manner described herein. Retinal image pre-processing tool 130 then determines 608 whether the portion of the retina is depicted in a third portion of the second image. That is, fallback image assessment module 333 determines whether another captured image includes a depiction of the same portion of the retina at some portion of the other captured image. For example, retinal image pre-processing tool 130 determines whether optic disc-centered left eye image 530 depicts that same portion of the retina that was insufficient in fovea-centered left eye image 510.

Retinal image pre-processing tool 130 determines 610 whether the third portion of the second image (e.g., a portion of the optic disc-centered left eye image 530 that captures the same portion of the retina as is insufficient in the fovea-centered left eye image 510) meets the criterion. Responsive to the third portion meeting the criterion, retinal image pre-processing tool 130 performs 612 the diagnosis using the plurality of retinal images (e.g., using image stitching module 335). Responsive to the third portion not meeting the criterion, retinal image pre-processing tool 130 captures 614 an additional image of the retinal region depicted in the first image (e.g., using image recapture module 334).

(g) Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

While the disclosure focuses on retinal disease specifically, the disclosure generally applies to disease diagnosis generally, and capture (and potential re-capture), as well as pre-processing of, images of other parts of a patient's body. For example, the disclosed pre-processing may apply to diagnosis of other organs, such as one's kidney, liver, brain, or heart, or portions thereof, and the images discussed herein may be of the relevant organs.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for minimizing exposure of a retina to flash during image gathering for diagnosis, the method comprising:
    capturing a first retinal image of a first retinal region by flashing the first retinal region responsive to determining a capturing device is focused on the first retinal region;
    capturing a second retinal image of a second retinal region by flashing the second retinal region responsive to determining the capturing device is focused on the second retinal region, the first retinal image and the second retinal image together forming a plurality of retinal images;
    determining whether to again flash the first retinal region by:
        determining that a first portion of the first retinal image does not meet a criterion while a second portion of the first retinal image does meet the criterion;
        identifying a portion of the retina depicted in the first portion that does not meet the criterion;
        determining whether the portion of the retina is depicted in a third portion of the second image;
        determining whether the third portion meets the criterion;
        responsive to determining that the third portion meets the criterion, determining to not again flash the first retinal region and to perform the diagnosis using the plurality of retinal images, wherein performing the diagnosis comprises passing the plurality of images to a fully autonomous machine learning model that outputs a likelihood of a disease condition based on the plurality of retinal images; and
    responsive to determining that the portion of the retina is not depicted in the second image, determining to again flash the first retinal region in connection with capturing an additional image of the first retinal region.

2. The method of claim 1, wherein capturing the first retinal image includes capturing a multi-frame video while the first retinal region is illuminated from the flashing of the first retinal region, the flashing of the first retinal reion caused by a single flash, each frame of the multi-frame video capturing an image at a different level of flash exposure.

3. The method of claim 1, wherein determining that the first portion of the first retinal image does not meet the criterion comprises determining that the first portion of the first retinal image is either over-exposed or under-exposed.

4. The method of claim 1, wherein the second retinal image is an image of the retina of a same eye that the first image depicts.

5. The method of claim 1, wherein performing the diagnosis using the plurality of retinal images comprises:
    generating a composite image comprising the first portion of the first retinal image with the third portion of the second retinal image stitched into the first retinal image; and
    performing the diagnosis using the composite image.

6. The method of claim 1, wherein performing the diagnosis using the plurality of retinal images comprises:
  analyzing the first retinal image while discounting the first portion to generate a first analysis;
  analyzing the third portion of the second retinal image to generate a second analysis; and
  performing the diagnosis using the first analysis and the second analysis.

7. The method of claim 1, wherein capturing the additional image comprises:
  transmitting, to an imaging device, using an application protocol interface (API), a command to capture an additional image using a perspective used to capture the first retinal image; and
  receiving the additional image from the imaging device.

8. The method of claim 1, wherein performing the diagnosis using the plurality of retinal images comprises using the third portion in the diagnosis.

9. A computer program product for minimizing exposure of a retina to flash during image gathering for diagnosis, the computer program product comprising a non-transitory computer-readable storage medium containing computer program code for:
  capturing a first retinal image of a first retinal region by flashing the first retinal region responsive to determining a capturing device is focused on the first retinal region;
  capturing a second retinal image of a second retinal region by flashing the second retinal region responsive to determining the capturing device is focused on the second retinal region, the first retinal image and the second retinal image together forming a plurality of retinal images;
  determining whether to again flash the first retinal region by:
    determining that a first portion of the first retinal image does not meet a criterion while a second portion of the first retinal image does meet the criterion;
    identifying a portion of the retina depicted in the first portion that does not meet the criterion;
    determining whether the portion of the retina is depicted in a third portion of the second image;
    determining whether the third portion meets the criterion;
    responsive to determining that the third portion meets the criterion, determining to not again flash the first retinal region and to perform the diagnosis using the plurality of retinal images; and
    responsive to determining that the portion of the retina is not depicted in the second image, determining to again flash the first retinal region in connection with capturing an additional image of the first retinal region.

10. The computer program product of claim 9, wherein the computer program code for performing the diagnosis comprises computer program code for passing the plurality of images to a fully autonomous machine learning model that outputs a likelihood of a disease condition based on the plurality of retinal images.

11. The computer program product of claim 9, wherein capturing the first retinal image includes capturing a multi-frame video while the first retinal region is illuminated from the flashing of the first retinal region, the flashing of the first retinal region caused by a single flash, each frame of the multi-frame video capturing an image at a different level of flash exposure.

12. The computer program product of claim 9, wherein the computer program code for determining that the first portion of the first retinal image does not meet the criterion comprises computer program code for determining that the first portion of the first retinal image is either over-exposed or under-exposed.

13. The computer program product of claim 9, wherein the second retinal image is an image of the retina of a same eye that the first image depicts.

14. The computer program product of claim 9, wherein the computer program code for performing the diagnosis using the plurality of retinal images comprises computer program code for:
  generating a composite image comprising the first portion of the first retinal image with the third portion of the second retinal image stitched into the first retinal image; and
  performing the diagnosis using the composite image.

15. The computer program product of claim 9, wherein the computer program code for performing the diagnosis using the plurality of retinal images comprises computer program code for:
  analyzing the first retinal image while discounting the first portion to generate a first analysis;
  analyzing the third portion of the second retinal image to generate a second analysis; and
  performing the diagnosis using the first analysis and the second analysis.

16. The computer program product of claim 9, wherein the computer program code for capturing the additional image comprises computer program code for:
  transmitting, to an imaging device, using an application protocol interface (API), a command to capture an additional image using a perspective used to capture the first image; and
  receiving the additional image from the imaging device.

17. The computer program product of claim 9, wherein performing the diagnosis using the plurality of retinal images comprises using the third portion in the diagnosis.

18. A computer program product for minimizing exposure of a retina to flash during image gathering for diagnosis, the computer program product comprising a non-transitory computer-readable storage medium containing computer program code that comprises:
  a first module for:
    capturing a first retinal image of a first retinal region by flashing the first retinal region responsive to determining a capturing device is focused on the first retinal region; and
    capturing a second retinal image of a second retinal region by flashing the second retinal region responsive to determining the capturing device is focused on the second retinal region, the first retinal image and the second retinal image together forming a plurality of retinal images;
  a second module for determining whether to again flash the first retinal region by:
    determining that a first portion of the first retinal image does not meet a criterion while a second portion of the first retinal image does meet the criterion;
    identifying a portion of the retina depicted in the first portion that does not meet the criterion;
    determining whether the portion of the retina is depicted in a third portion of the second image; and
    determining whether the third portion meets the criterion;

a third module for, responsive to determining that the third portion meets the criterion,
   determining to not again flash the first retinal region and to perform the diagnosis using the plurality of retinal images; and
a fourth module for, responsive to determining that the portion of the retina is not depicted in the second image, determining to again flash the first retinal region in connection with capturing an additional image of the first retinal region.

19. The computer program product of claim 18, wherein performing the diagnosis comprises passing the plurality of retinal images to a fully autonomous machine learning model that outputs a likelihood of a disease condition based on the plurality of retinal images.

\* \* \* \* \*